US009302241B2

(12) United States Patent
Benoit et al.

(10) Patent No.: US 9,302,241 B2
(45) Date of Patent: Apr. 5, 2016

(54) METHOD OF PREPARING LIPID NANOPARTICLES

(75) Inventors: Jean-Pierre Benoit, Angers (FR); Olivier Thomas, Angers (FR); Patrick Saulnier, Marigne (FR); Alyaa Adel Ramadan, Alexandrie (EG)

(73) Assignees: UNIVERSITE D'ANGERS, Angers (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 561 days.

(21) Appl. No.: 13/139,401

(22) PCT Filed: Dec. 11, 2009

(86) PCT No.: PCT/FR2009/052500
§ 371 (c)(1),
(2), (4) Date: Sep. 23, 2011

(87) PCT Pub. No.: WO2010/067037
PCT Pub. Date: Jun. 17, 2010

(65) Prior Publication Data
US 2012/0027825 A1 Feb. 2, 2012

(30) Foreign Application Priority Data

Dec. 12, 2008 (FR) ...................... 08 58547

(51) Int. Cl.
*A61K 9/50* (2006.01)
*B01J 13/04* (2006.01)
(52) U.S. Cl.
CPC ...................... *B01J 13/04* (2013.01)
(58) Field of Classification Search
None
See application file for complete search history.

(56) References Cited

U.S. PATENT DOCUMENTS

| 5,576,016 | A | 11/1996 | Amselem et al. | |
|---|---|---|---|---|
| 5,961,970 | A | 10/1999 | Lowell et al. | |
| 5,961,971 | A | 10/1999 | Martin | |
| 2003/0152635 | A1* | 8/2003 | Heurtault et al. | 424/490 |
| 2009/0238865 | A1 | 9/2009 | Heurtault et al. | |
| 2010/0233275 | A1 | 9/2010 | Saulnier et al. | |
| 2010/0266676 | A1 | 10/2010 | Saulnier et al. | |

FOREIGN PATENT DOCUMENTS

| EP | 1 955 695 | 8/2008 |
|---|---|---|
| FR | 2 840 532 | 12/2003 |
| WO | WO91/18669 | * 12/1991 |
| WO | 01 64328 | 9/2001 |
| WO | 03 103822 | 12/2003 |
| WO | 2009 001019 | 12/2008 |
| WO | 2009 004214 | 1/2009 |

OTHER PUBLICATIONS

Pitaksuteepong et al.,Factors influencing the entrapment of hydrophilic compounds in nanocapsules prepared by interfacial polymerisation of water-in-oil microemulsions, European Journal of Pharmaceutics and Biopharmaceutics, 53(3), 2002, pp. 335-342.*
U.S. Appl. No. 13/260,168, filed Sep. 23, 2011, Benoit et al.
Beduneau, A. et al., "Pegylated Nanocapsules Produced by an Organic Solvent-Free Method: Evaluation of Their Stealth Properties", Pharmaceutical Research, vol. 23, No. 9, pp. 2190-2199, XP002539233, (Aug. 9, 2006).
Heurtault, B. et al., "A Novel Phase Inversion-Based Process for the Preparation of Lipid Nanocarriers", Pharmaceutical Research, vol. 19, No. 6, pp. 875-880, XP002539234, (Jun. 2002).
Cadene, M. et al., "Influence of Low Molecular Mass Heparin on the Kinetics of Neutrophil Elastase Inhibition by Mucus Proteinase Inhibitor", The Journal of Biological Chemistry, vol. 270, No. 22, pp. 13204-13209, (Jun. 2, 1995).
Shinoda, K. et al., "The Stability of O/W Type Emulsions as Functions of Temperature and the HLB of Emulsifiers: The Emulsification by PIT-Method", Journal of Colloid and Interface Science, vol. 30, No. 2, pp. 258-263, (Jun. 1969).
Patel, N. et al., "Phospholipid-Based Microemulsions Suitable for Use in Foods", J. Agric. Food Chem, vol. 54, pp. 7817-7824, (2006).
Boonme, P., "Applications of Microemulsions in Cosmetics", Journal of Cosmetic Dermatology, vol. 6, pp. 223-228, (2007).
Shinoda, K., Journal of the Chemical Society of Japan, vol. 89, pp. 435-442, (1968).
International Search Report Issued Mar. 1, 2010 in PCT/FR09/052500 filed Dec. 11, 2009.

* cited by examiner

*Primary Examiner* — Bethany Barham
*Assistant Examiner* — Melissa Javier
(74) *Attorney, Agent, or Firm* — Oblon, McClelland, Maier & Neustadt, L.L.P.

(57) ABSTRACT

Provided is a method for preparing nanocapsules having a liquid lipid core and a solid shell and charged in their lipid core with at least one hydrophilic active agent involving combining microemulsions where the active agent remains in the hydrophilic phase of a first microemulsion and chill-hardening the mixture to obtain the nanocapsules charged with the hydrophilic active agent. The nanocapsules comprise the lipid core which is liquid at room temperature and the nanocapsules are encapsulated in a film which is solid at room temperature.

19 Claims, 4 Drawing Sheets

METHOD OF PREPARING LIPID NANOPARTICLES

CROSS REFERENCE TO RELATED APPLICATIONS

The present application is a 35 U.S.C. §371 national stage patent application of International patent application PCT/FR09/052500, filed on Dec. 11, 2009, the text of which is incorporated by reference, and claims the benefit of the filing date of French application no. 0858547, filed on Dec. 12, 2008, the text of each also being incorporated by reference.

BACKGROUND OF THE INVENTION

Field of the Invention

The present invention relates to a useful method for preparing lipid nanocapsules charged with at least one active agent and also to such nanocapsules and the compositions containing them.

Description of the Background

Nanovesicular systems, of nanocapsule or nanodroplet type whose size ranges from 50 to 500 nanometers and which are formed from a liquid or semisolid core surrounded by an outer membrane, are already known. The constituents of their membrane may be synthetic, for example of polymeric, protein or lipid nature like liposomes. Notably, liposomes that have a lamellar structure formed from a stack of lipid layers separated from each, other by aqueous compartments always have an aqueous core.

These nanometric structures have also already been proposed for the purposes of encapsulating active agents either in their aqueous core when the active agent is water-soluble or water-dispersible, or in their lipid layer when the active agent is fat-soluble or fat-dispersible.

For example, U.S. Pat. No. 5,961,970 proposes, as active agent vehicle, oil-in-water emulsions at the submicron scale, i.e. miniemulsions whose droplets have a hydrophobic core of lipid nature and are surface-stabilized with amphiphilic and/or nonionic surfactants like surfactants of phospholipid type. These droplets are thus maintained in suspension in an aqueous phase. This type of submicron emulsion is obtained from a basic emulsion by subjecting it to several successive homogenization cycles at high shear.

U.S. Pat. No. 5,576,016 describes macroemulsions whose droplets are formed from a solid lipid core and which are stabilized with a phospholipid envelope. This phospholipid envelope has a lamellar structure formed from one or more layers of phospholipid molecules like liposomes. A highly hydrophobic active agent may be charged into the core, and a water-soluble active agent may, on the other hand, be incorporated into the aqueous compartments present in the phospholipid envelope.

Moreover, the inventors have also described in patent EP 1 265 698, as vehicle for fat-soluble or fat-dispersible active agents, nanocapsules with a liquid core and a solid shell of lipid nature, and novel technology for gaining access thereto. More specifically, these nanocapsules, charged with fat-soluble or fat-dispersible active agents, are obtained from a microemulsion, this microemulsion being prepared via the technique of phase inversion via a thermal effect (PIT emulsion).

The principle of phase inversion temperature (PIT) emulsification is well known to those skilled in the art; it was described in 1968 by K. Shinoda (J. Chem. Soc. Jpn, 1968, 89, 435). It was shown that this emulsification technique makes it possible to obtain fine stable emulsions (K. Shinoda and H. Saito, J. Colloid Interface Sci., 1969, 30, 258).

This technique makes it especially possible to obtain a mean size of the globules constituting the oily phase ranging from 0.1 to 4 µm (100 to 4000 nm).

However, when these nanocapsules are intended for encapsulating an active agent, this method necessitates having the active substance that it is desired to encapsulate being present right from the first step of the method and therefore the entire method must be carried out in the presence of this active agent. However, this obligation may sometimes be constricting to a person skilled in the art.

Moreover, the nanocapsules obtained have been proposed therein only for the purpose of encapsulating, within their oily core, lipophilic or fat-dispersible active agents. Now, for obvious reasons, it would be advantageous for these nanocapsules also to be usefully employed for encapsulating water-soluble or water-dispersible active agents.

Thus, a person skilled in the art does not have a simple and rapid method of implementation for obtaining nanocapsules charged with active agents, especially active agents having a hydrophilic character and, what is more, a method having an advantageous encapsulation yield.

SUMMARY OF THE INVENTION

The object of the present invention is specifically to provide a novel method for satisfying this need.

More precisely, the invention relates, according to a first of its aspects, to a useful method for preparing nanocapsules having a liquid lipid core and a solid shell and charged with at least one active agent having a hydrophilic character, said method comprising at least the steps consisting in:

i) providing at least a first microemulsion having a water-in-oil character, stabilized by at least one lipophilic surfactant and containing in its hydrophilic phase at least one active agent having a hydrophilic character;

ii) providing at least a second microemulsion, separate from the first microemulsion, formulated by phase inversion of an emulsion and stabilized by at least one heat-sensitive, nonionic hydrophilic surfactant;

iii) adding said first microemulsion to said second microemulsion under conditions propitious for the formation of a novel microemulsion architecture in which said hydrophilic active agent remains present in the hydrophilic phase of the first microemulsion; and iv) chill-hardening the mixture formed in the previous step, so as to obtain nanocapsules comprising said hydrophilic active agent and being formed from a lipid core, which is liquid at room temperature, and encapsulated in a film which is solid at room temperature.

DETAILED DESCRIPTION OF THE INVENTION

According to one particular embodiment, the hydrophilic active agent formulated using the method according to the invention is, after said method has been implemented, present in the liquid lipid core of said nanocapsules.

According to another particular embodiment, the invention relates to the aforementioned method in which the second microemulsion is, before mixing, a water-in-oil microemulsion.

In the context of the present invention, the term "hydrophilic character" means that the active agent has a predominant affinity for water or an aqueous medium.

A hydrophilic compound may therefore in particular be a water-soluble compound or else a water-dispersible compound.

In the context of the present invention, the term "hydrophilic phase" or "polar phase" is understood to mean a medium completely or partially formed from water. Thus, it may be formed completely or partly from water, completely or partly from at least one polar solvent, or from a water/polar solvent mixture.

According to another of its aspects, the present invention relates to nanocapsules that can be obtained by said method according to the present invention.

The invention also relates to nanocapsules having a liquid lipid core and a solid shell, these being charged within their liquid lipid core with at least one active agent having a hydrophilic, in particular water-soluble, character, said active agent being present in the liquid lipid core in the form of hydrophilic microdomains or of a microemulsion having a water-in-oil character comprising an oily phase stabilized by at least one lipophilic surfactant and a hydrophilic phase incorporating said active agent.

The invention also relates to compositions containing such nanocapsules.

The present invention relates more particularly from the observation by the inventors that, against all expectation, a microemulsion obtained by phase inversion of an emulsion, in particular using the PIT (phase inversion temperature) technique, proves to be capable of interacting with an ancillary microemulsion of water-in-oil character and containing, in its hydrophilic or else polar phase, at least one hydrophilic active agent so as to form a microemulsion-type architecture containing said active agent in its internal hydrophilic micellar structure.

Surprisingly, the required interaction according to the invention between the two microemulsions does not prejudice, in terms of stability, the polar microdomains or even the micellar structures containing the hydrophilic active agent present in the first microemulsion. These microdomains are held within oil droplets dedicated to forming the liquid lipid core of the nanocapsules during chill-hardening.

MICROEMULSIONS

Firstly, it is important to note that a microemulsion is different from a miniemulsion or nanoemulsion and from a macroemulsion, especially as illustrated in U.S. Pat. No. 5,961,971 and U.S. Pat. No. 5,576,016, and which are termed two-phase systems. Specifically a microemulsion corresponds to a bi-continuous structuring of the material in the form of micellar structures swollen with oil or water. These micellar structures are highly mutually interlinked and thus constitute a homogeneous, cohesive, stabilized three-dimensional network. Thus, the microemulsions have microdomains that are not necessarily spherical, are small in size, typically ranging from about 10 to 50 nm, fluctuating in time and in space.

In other words, the microemulsions are not emulsions consisting of mini-droplets. It is not possible to distinguish therein the dispersed phase from the continuous phase. Finally, unlike macroemulsions, miniemulsions and nanoemulsions, microemulsions are thermodynamically stable. Such microemulsions are described in particular by Patel et al., "*J. Agric. Food Chem.*" 2006, 54, 7817-7824.

A person skilled in the art knows that formulating microemulsions amounts to choosing variables of two types: compositional variables and physicochemical formulation variables.

The term "compositional variables" refers to the relative proportions of the principal constituents of the system, namely the surfactant system, the hydrophilic or polar phase and the oily phase.

The physicochemical formulation variables include, for their part, all the other physical parameters (temperature, pressure) or chemical parameters (nature of the principal constituents and of the additives) liable to have an influence on the system.

To adjust these parameters necessary for forming the expected microemulsion, one standard technique is to generate a corresponding phase diagram.

Figure 1:
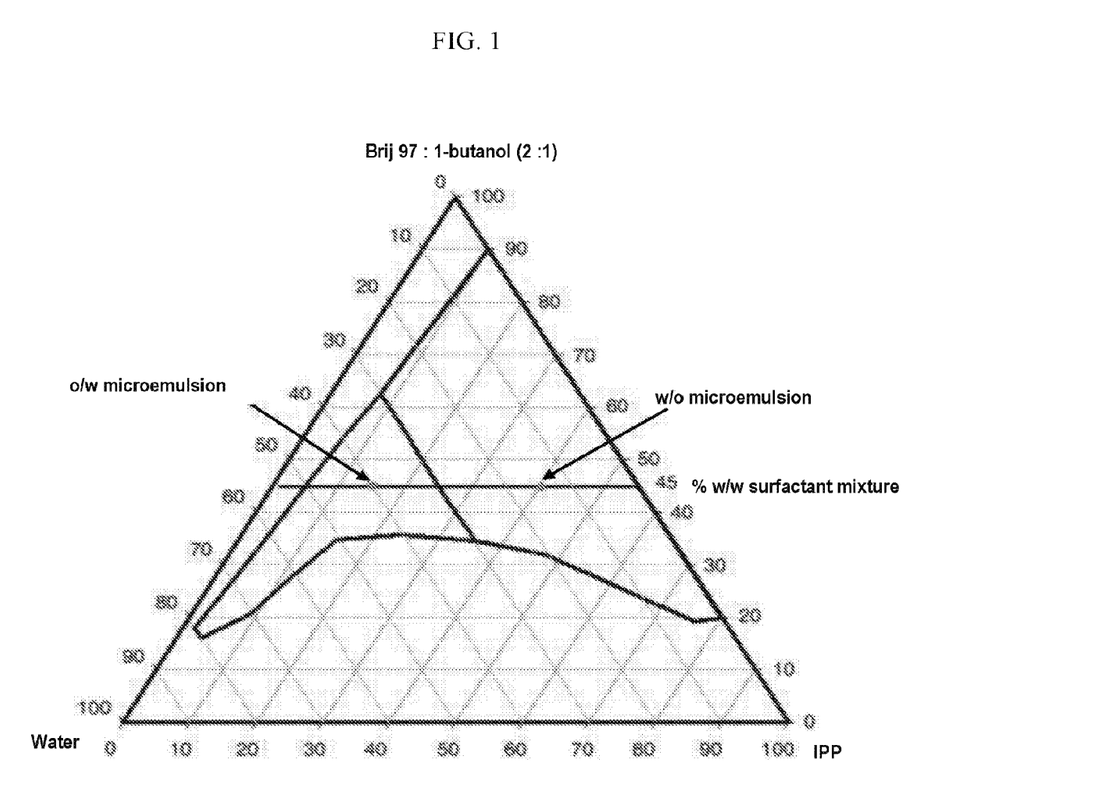
FIG. 1: example of a ternary phase diagram of a microemulsion system.

Such a diagram may be generated using various methods, the simplest of which consists in titrating a mixture of two components in question with the third component. FIG. 1, taken from the article by Prapapom Boonme, "*Journal of Cosmetic Dermatology*", 2007, 6, 233-228, illustrates an example of a ternary phase diagram of a microemulsion system.

Once the phase diagram has been generated, the microemulsion zone is identified and a microemulsion may be easily prepared simply by mixing the required components in one of the specific ratios that exist in this microemulsion zone.

As will be apparent from this diagram, the microstructure of a microemulsion may be described as having a bi-continuous oil-in-water (O/W), or water-in-oil (W/O) character depending on the relative quantity of each of the components present.

It is also known to characterize these systems by Winsor's ratio R that specifies the interactions of the surfactant molecules located at the interface with the neighboring molecules of the oily phase and of the hydrophilic phase according to the equation:

$$R = A_{SO}/A_{SW}$$

where A denotes the molecular interactions per unit interfacial area and W, O, and S are the indices referring to the hydrophilic phase, the oily phase and the surfactant respectively.

Figure 2:
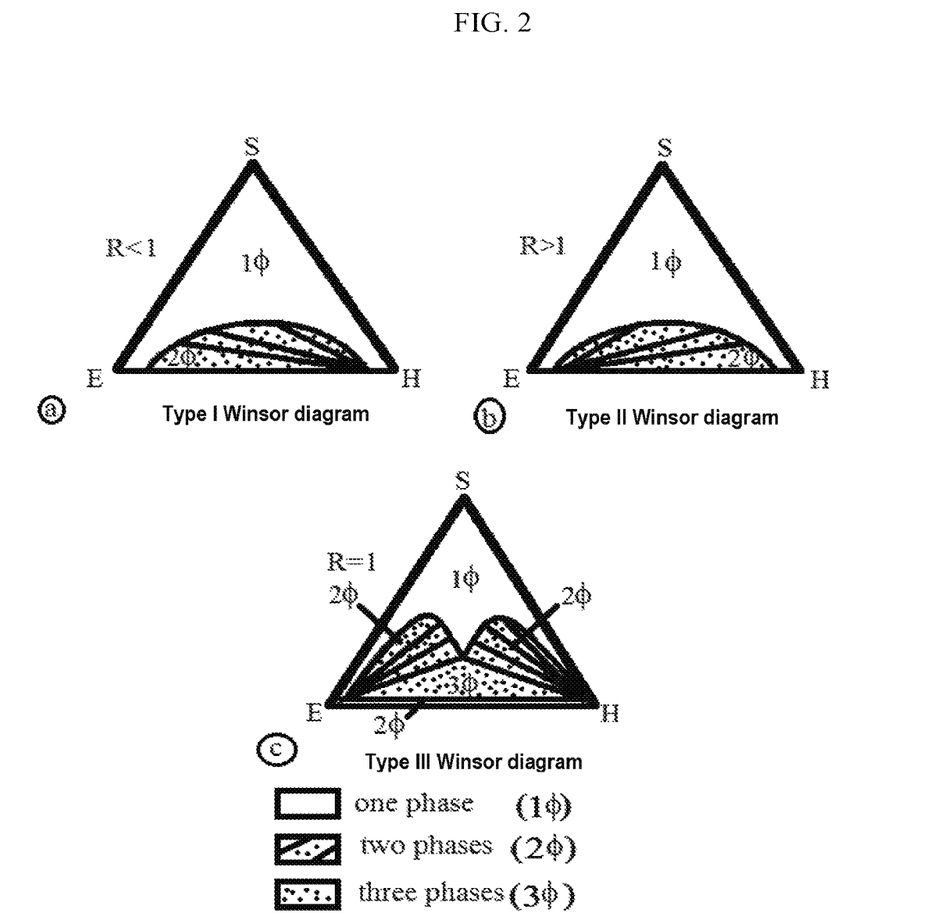
FIG. 2: Type I, II and III Winsor phase diagrams.

According to whether the ratio R is less than, greater than or equal to the unit, characteristic phase diagrams called Winsor I, II or III, respectively, are obtained, such as those shown in FIG. 2. Moreover, the clear single-phase phases of these diagrams are termed Winsor IV microemulsions. In the majority of cases, the limits of the zone of this type of microemulsion are shown by the appearance of a cloudy solution.

Thus, starting from a certain surfactant concentration, between 10% and 50%, the polyphase zone disappears and the surfactant "co-dissolves" the hydrophilic phase and the oily phase in the form of relatively organized structures such as microemulsions or liquid-crystal phases (single-phase zone). The lines drawn in the two-phase zone shown in this FIG. 2 are called conjugation or partition lines.

The inclination of the partition lines indicates that most of the surfactant is in the aqueous phase in the case of Winsor I and in the oily phase in the case of Winsor II.

In the case of the Winsor III diagram, there is a zone lying within a triangle where the system separates into three phases, namely a microemulsion containing practically all the surfactant and two other phases formed in the hydrophilic phase and the oily phase.

However, at high surfactant concentration, a single-phase zone, the behavior of which is referred to as being of the Winsor IV type, is always observed, In other words, a Winsor IV representation corresponds to the single-phase part of one of the Winsor I, II and III diagrams of FIG. 2.

Microemulsion Containing the Hydrophilic Active Agent

As mentioned above, the first microemulsion may comprise at least one oily fatty phase, at least one lipophilic surfactant, a polar or hydrophilic phase, and may contain, in its polar or hydrophilic phase, at least one active agent having a hydrophilic character, in particular a water-soluble or even water-dispersible active agent.

According to a preferred embodiment, this microemulsion also exhibits Winsor IV behavior.

Advantageously, this microemulsion has a water-in-oil character.

a—Oily Phase

The oily phase is formed from at least one fatty substance that is liquid or semiliquid at room temperature, and in particular from at least one triglyceride, a fatty acid ester, or a mixture thereof.

The fatty acid ester may be chosen more particularly from $C_4$ to $C_{18}$, especially $C_8$ to $C_{12}$, and more particularly $C_8$ to $C_{10}$ fatty acid esters and especially tributyrine, ethyl palmitate, ethyl oleate, ethyl myristate, isopropyl myristate, octyldodecyl myristate, and mixtures thereof.

The triglycerides used may be synthetic triglycerides or triglycerides of natural origin. The natural sources may include animal fats or plant oils, for example soybean oils or sources of long-chain triglycerides (LCT).

Other triglycerides of interest are composed mainly from medium-length fatty acids, also known as medium-chain triglycerides (MCT). A medium-chain triglyceride (MCT) oil is a triglyceride in which the carbohydrate chain contains from 8 to 12 carbon atoms.

Such MCT oils are commercially available.

As examples of these MCT oils, mention may be made of the TCR products (commercial name from the Société Industrielle des Oléagineux, France, for a triglyceride mixture in which about 95% of the fatty acid chains contain 8 or 10 carbon atoms) and Myglyol® 812 (triglyceride sold by the company Dynamit Nobel, Sweden, for a mixture of caprylic and capric acid glyceride triesters).

The fatty acid units of these triglycerides may be unsaturated, monounsaturated or polyunsaturated. Mixtures of triglycerides containing variable fatty acid units are also acceptable.

It should be noted that the higher the HLB value of the liquid or semiliquid fatty substance, the higher the phase inversion temperature. On the other hand, the HLB value of the fatty substance does not appear to have an influence on the size of the nanocapsules.

Thus, when the size of the end groups of the triglycerides increases, their HLB value decreases and the phase inversion temperature decreases.

The HLB value, or hydrophilic-lipophilic balance, is such as defined by C. Larpent in Traité K.342 of the Editions Techniques de l'Ingénieur.

The triglyceride sold under the name Labrafac WL 1349® or Labrafac® CC is most particularly suitable for use in the invention.

b—Hydrophilic or Polar Phase

As regards the hydrophilic or polar phase, this may or may not be an aqueous phase. Thus, it may be formed entirely or partly from water, entirely or partly from at least one polar solvent or from a water/polar solvent mixture.

Advantageously, the hydrophilic phase consists solely of water.

According to another embodiment, the hydrophilic phase may be free of water. In this case, it may be formed from at least one hydrophilic solvent. Such a polar solvent is chosen for its ability to dissolve the active agent in question and, in respect of the intended application (in a human or animal) for its innocuousness. Thus, a person skilled in the art is capable of choosing such a solvent.

Such polar solvents may, for example, be chosen from polypropylene glycols, propylene glycol, ethanol, isopropanol, glycerol, glycofurol, low-molecular-weight polyethylene glycols, polyols, and mixtures thereof. For example, such a hydrophilic phase may consist only of propylene glycol [Patel et al, "*J. Agric. Food Chem.*" 2006, 54, 7817-7824].

According to another embodiment, the hydrophilic phase may be formed completely or partially from water.

More particularly, this may be a mixture of water and one or more polar solvents, said polar solvents being as defined above.

It is understood that certain polar solvents may also possess surface-active properties. It may then be necessary to take account of these properties when producing the microemulsion. The solvent in question will then have two functions, that of a solvent and that of a co-surfactant, or indeed in certain cases an essentially co-surface-active function.

According to one particular embodiment, such a mixture may comprise 0.1% to 50% water and 50% to 99.9% of at least one polar solvent.

According to another particular embodiment, such a mixture may comprise 0.1% to 50% of at least one polar solvent and 50% to 99.9% water.

According to another embodiment, such a mixture may be a water/propylene glycol mixture that may be formed from 10% to 45% water, preferably 15% to 35%, and more particularly 20% to 30% water, or even about 25% water, and 50% to 95% of propylene glycol, preferably 55% to 85%, more particularly 70% to 80%, for example about 75% of propylene glycol.

According to another particular embodiment, said mixture is an equimolar mixture.

According to another embodiment, the hydrophilic phase may further include a co-surfactant, especially one having a hydrophilic character. Such co-surfactants are well known to those skilled in the art. They may, for example be long alcohols, butanol, pentanol, hexanol, and mixtures thereof. Other examples are mentioned in Patel et al. (ibid).

It should be understood that this first microemulsion may further include, where appropriate, a lipophilic active agent, in particular a fat-soluble, or even fat-dispersible active agent. This will then be retained within the lipid phase thereof.

c—Surfactants

As mentioned above, the first microemulsion containing at least one hydrophilic active agent is stabilized by at least one lipophilic surfactant.

For obvious reasons, the nature of the surfactant necessary for stabilizing the microemulsion is directly dependent on the chemical nature of the hydrophilic and lipophilic phases brought into contact with each other.

Thus, in the case of contacting with a hydrophilic phase formed essentially from a solvent such as propylene glycol, the corresponding microemulsion may be effectively stabilized by a single lipophilic surfactant.

However, if the hydrophilic phase comprises water, whether or not in combination with an ancillary polar solvent, it may be necessary to add a co-surfactant to the lipophilic surfactant.

The lipophilic surfactant may or may not be solid at room temperature.

The lipophilic surfactant employed according to the present invention is more particularly based on phospholipids that are advantageous with regard to their biocompatible nature.

Among the phospholipids, phosphatidylcholines (lecithin) are particularly advantageous.

Other phospholipids may be phosphatidylglycerol, phosphatidylinositol, phosphatidylserine, phosphatidic acid and phosphatidylethanolamine.

The phospholipid derivatives may be isolated from natural sources or prepared via synthesis.

As commercial products derived from phospholipids, mention may be made more particularly of:
  Epicuron 120 (Lukas Meyer, Germany), which is a mixture of about 70% phosphatidylcholine, 12% phosphatidylethanolamine and about 15% other phospholipids;
  Ovotine 160® (Lukas Meyer, Germany), which is a mixture comprising about 60% phosphatidylcholine, 18% phosphatidylethanolamine and 12% other phospholipids,
  a mixture of purified phospholipids such as the products Lipoid E75 or Lipoid E80® (Lipoid, Germany), which is a mixture of phospholipids comprising about 80% by weight of phosphatidylcholine, 8% by weight of phosphatidylethanolamine, 3.6% by weight of nonpolar lipids and 2% of sphingomyelin.

According to one preferred embodiment, the lipophilic surfactant is a lecithin whose proportion of phosphatidylcholine ranges from 40% to 80% by weight.

Lipoid S75-3® (Lipoid GmbH, Germany) is most particularly suitable as a source of phosphatidylcholine. It is soybean lecithin. This product contains about 69% phosphatidylcholine and 9% phosphatidylethanolamine. This constituent is the only constituent that is solid at 37° C. and at room temperature in the formulation.

Polyglyceryl-6 dioleate (Plurol®) may also be used.

It is also possible to use, as fat-soluble surfactant suitable for the present invention, sucrose esters, such as saccharose and fatty acid esters, alkyl glucose esters, particularly polyoxyethylenated $C_1$-$C_6$ alkyl glucose fatty esters and mixtures thereof.

More particularly mention may be made of sucrose monostearate or distearate and sucrose polystearates having especially a high proportion of sucrose monostearate.

For obvious reasons, the oily phase, hydrophilic phase, and surfactant portions are to be adjusted, with regard to the chemical nature of the specific compounds employed, in order to obtain a microemulsion. This adjustment is made via the generation of a phase diagram, which it is clearly within the competence of a person skilled in the art to produce. Example 1, given below, provides a specific way of forming such an emulsion. Moreover, FIGS. 3 and 4, each providing an example of a phase diagram, illustrate several examples of first microemulsions.

According to one embodiment, the first microemulsion is formed from at least a fatty acid triglyceride, a lecithin, a 2-hydroxystearate derivative of polyethylene glycol and a hydrophilic active agent.

The first microemulsion may be produced at various temperatures, these depending directly on the choice of the components required to form its microemulsion architecture, namely the oily phase, the hydrophilic or polar phase and the surfactants.

It should be noted that the hydrophilic phase containing the hydrophilic active agent forms, within the microemulsion, microdomains having a size that may be precisely adjusted through the temperature retained to form said microemulsion. This size is advantageously less than 50 nm.

d—Active Agent

As indicated above, the method is particularly advantageous for internalizing, within the nanocapsules having a lipid core, a hydrophilic active agent, i.e. one which is water-soluble or water-dispersible.

According to a preferred embodiment, this active agent is water-soluble.

The hydrophilic active agent is formulated according to the invention via the first water-in-oil microemulsion which incorporates it within its hydrophilic micellar structure.

In other words, the active agent having a hydrophilic, or even water-soluble, active agent is contained in polar or hydrophilic microdomains, stabilized by at least one lipophilic surfactant in the oily phase.

Its prior incorporation into this first microemulsion is achieved by dissolving said active agent in the hydrophilic phase intended to form the microemulsion.

At the same time, the surfactants, including at least one lipophilic surfactant and the oily phase, are mixed beforehand and, once, the surfactants have been dissolved in the oil, the two phases, the oily phase and the aqueous phase, are brought into contact with each other.

The whole assembly is heated to a temperature propitious for producing the expected microemulsion.

This temperature ranges from room temperature to 75° C.

Thus, according to one particular embodiment, in the method according to the present invention, the first microemulsion considered for the mixture is, during mixing, at a temperature ranging from room temperature to 75° C.

This temperature is generally adjusted so as to enable all of the constituents to be uniformly mixed. This adjustment is particularly advisable when one of the compounds is solid at room temperature, such as, for example, certain phospholipid surfactants. Thus, by using S75-3 Lipoid® as surfactant, to form the microemulsion, the mixture has to be heated to a temperature above 72° C., i.e. the melting point of the lipoid.

The temperature of the mixture may advantageously be maintained until it is introduced into the second microemulsion.

However, the whole system may, where appropriate, also be placed at room temperature or in an oven at 37° C. until it clears. This embodiment proves to be most particularly advantageous in the case of active agents having a heat-sensitive hydrophilic character.

Of course, the method according to the invention is also compatible with the formulation of one or more lipophilic active agents, i.e. one or more fat-soluble or fat-dispersible active agents.

This lipophilic active agent may be introduced via the lipid micellar structure of the first or second microemulsion.

Advantageously, when the active agent is lipophilic, it is introduced via the second microemulsion.

The relevant active agents according to the invention may be a pharmaceutically active or cosmetically active compound or a compound that is active in the plant protection or food sector.

According to a preferred embodiment, this active agent is a pharmaceutically active principle.

Such an active agent may also be of protein or peptide nature. It may also be a nucleic acid such as a DNA plasmid or interference RNA.

The active agent may also be a radiopharmaceutical agent. It may also be a gas or a fluid that can be converted into a gas.

Second Microemulsion

As mentioned above, the second microemulsion is stabilized by at least one heat-sensitive hydrophilic surfactant.

This microemulsion may be of a water-in-oil character (right-hand part of the phase inversion zone or PIZ) or an oil-in-water character (left-hand part of the PIZ).

Advantageously, it is of the water-in-oil type.

Thus, according to one particular embodiment of the present invention, the second microemulsion before mixing is a water-in-oil microemulsion.

The emulsifying surfactants normally used have an HLB (hydrophilic-lipophilic balance) value ranging from 8 to 18. These emulsifiers, by virtue of their amphiphilic structure, are positioned at the oily phase/aqueous phase interface, and thus stabilize the dispersed oil droplets.

These surfactants are generally termed heat-sensitive, hydrophilic nonionic surfactants.

The choice of such a surfactant proves particularly advantageous in order to ensure that the phase inversion operation takes place by a temperature variation, leading to a microemulsion architecture.

Thus, the solubility in oil of this type of surfactant, used in the second microemulsion according to the invention, increases as the temperature increases. The HLB of such surfactants may range from 8 to 18, preferably from 10 to 18, especially from 10 to 16. According to one embodiment of the invention, such surfactants may be chosen from ethoxylated fatty alcohols, ethoxylated fatty acids, partial glycerides of ethoxylated fatty acids, fatty acid triglycerides and ethoxylated derivatives thereof, and mixtures thereof.

Examples of ethoxylated fatty alcohols that may be mentioned include adducts of ethylene oxide with lauryl alcohol, especially those comprising from 9 to 50 oxyethylene groups (Laureth-9 to Laureth-50 in CTFA names); adducts of ethylene oxide with behenyl alcohol, especially those comprising from 9 to 50 oxyethylene groups (Beheneth-9 to Beheneth-50 in CTFA names); adducts of ethylene oxide with cetostearyl alcohol (mixture of cetyl alcohol and stearyl alcohol), especially those comprising from 9 to 30 oxyethylene groups (Ceteareth-9 to Ceteareth-30 in CTFA names); adducts of ethylene oxide with cetyl alcohol, especially those comprising from 9 to 30 oxyethylene groups (Ceteth-9 to Ceteth-30 in CTFA names); adducts of ethylene oxide with stearyl alcohol, especially those comprising from 9 to 30 oxyethylene groups (Steareth-9 to Steareth-30 in CTFA names); adducts of ethylene oxide with isostearyl alcohol, especially those comprising from 9 to 50 oxyethylene groups (Isosteareth-9 to Isosteareth-50 in CTFA names); and mixtures thereof.

Examples of ethoxylated fatty acids that may be mentioned include the adducts of ethylene oxide with lauric, palmitic, stearic or behenic acid, and mixtures thereof, especially those comprising from 9 to 50 oxyethylene groups, such as PEG-9 to PEG-50 laurates (CTFA names: PEG-9 laurate to PEG-50 laurate); PEG-9 to PEG-50 palmitates (CTFA names: PEG-9 palmitate to PEG-50 palmitate); PEG-9 to PEG-50 stearates (CTFA names: PEG-9 stearate to PEG-50 stearate); PEG-9 to PEG-50 palmitostearates; PEG-9 to PEG-50 behenates (CTFA names: PEG-9 behenate to PEG-50 behenate); and mixtures thereof.

Mixtures of these oxyethylenated derivatives of fatty alcohols and of fatty acids may also be used.

These surfactants may also be either natural compounds such as echolate phospholipids or synthetic compounds such as polysorbates, which are polyethoxylated fatty acid esters of sorbitol (Tween®), polyethylene glycol esters and diglyceride esters originating, for example, from castor oil (Cremophor®), polyethoxylated fatty acids, for example of stearic acid (Simulsol M-53®), polyoxyethylenated fatty alcohol ethers (Brij®), polyoxyethylenated nonphenyl ethers (Triton N®) and polyoxyethylenated hydroxyphenyl ethers (Triton X®).

It may more particularly be a polyethylene glycol 2-hydroxystearate and especially the product sold under the name Solutol® HS15 by the company BASF (Germany).

According to another embodiment, the second microemulsion considered according to the present invention may furthermore contain a co-surfactant. More particularly, this co-surfactant has a lipophilic character.

It should be noted that the particle size of the microemulsion decreases when the proportion of hydrophilic surfactant increases and when the proportion of hydrophilic and lipophilic surfactants increases. Specifically, the hydrophilic surfactant causes a reduction in the interfacial tension and therefore stabilizes the system, thereby promoting the formation of small particles.

Moreover, the particle size increases when the proportion of oil increases.

For its part, the aqueous phase of the microemulsion may also advantageously contain 1 to 4% of a salt, especially a mineral salt such as, for example, sodium chloride. Specifically, modifying the salt concentration leads to a shift in the phase inversion zone. Thus, the higher the salt concentration, the lower the phase inversion temperature. This phenomenon proves to be most particularly advantageous for encapsulating hydrophobic heat-sensitive active principles.

According to one particular embodiment, the first microemulsion containing the active agent according to the invention may also contain such a salt, so as to maintain, if necessary, the same osmolarity upon introducing the first microemulsion into the second.

According to one particular embodiment, the second microemulsion advantageously contains 5 to 15% of hydrophilic surfactant(s), 5 to 15% of an oily phase, where appropriate combined with 1 to 3% of lipophilic surfactant(s) and 64 to 89% of an aqueous phase (the percentages being expressed by weight relative to the total weight of the microemulsion).

In a preferred embodiment, the fatty phase is a fatty acid triglyceride, the lipophilic surfactant is a lecithin and the hydrophilic surfactant is Solutol® HS15.

A microemulsion most particularly suitable for the invention can be obtained using the phase inversion technique, in particular by a temperature-mediated phase inversion operation starting from an oil-in-water emulsion stabilized by the surfactant system in question for the microemulsion. This technology is more particularly described in patent EP 1 265 698, the content of which is incorporated in the present application.

The second microemulsion is generally obtained while maintaining constant mechanical stirring.

Thus, all the constituents intended to form the second microemulsion are weighed out in a container. The mixture is homogenized, for example using a Rayneri blender at 350 rpm, and heated by gradually raising the temperature using a water bath up to a temperature greater than or equal to the phase inversion temperature $T_2$, i.e. until a more viscous white phase is obtained, indicating that the reverse (W/O) emulsion has been obtained. The heating is then stopped and stirring is maintained until the emulsion has cooled down to room temperature, passing through the phase inversion temperature $T_1$, i.e. the temperature at which the expected microemulsion forms, taking the form of a transparent or translucent phase. When the temperature has fallen back below the phase inversion temperature zone ($T_1$), an oil-in-water emulsion is obtained.

More precisely, the phase inversion between the oil/water emulsion and water/oil emulsion is manifested by a reduction in the conductivity, as the temperature increases, until it becomes zero.

Thus, $T_1$ is a temperature at which the conductivity is at least equal to 90-95% of the conductivity measured at 20° C. and $T_2$ is the temperature at which the conductivity becomes zero and the water-in-oil emulsion forms. The mean temperature of the phase inversion zone corresponds to the PIT (phase inversion temperature).

In the zone in which a microemulsion (translucent mixture) forms, hydrophilic and hydrophobic interactions are in balance since the tendency of the surfactant system is to form both direct micelles and reverse micelles. By heating beyond this zone, a W/O emulsion (opaque white mixture) forms, since the surfactant promotes the formation of a water-in-oil emulsion. Then, upon cooling below the phase inversion zone, the emulsion becomes an O/W emulsion.

Where appropriate, one or more temperature cycles around the phase inversion zone between $T_1$ and $T_2$ may be performed until a translucent suspension is observed, this corresponding to the formation of a new microemulsion. The system is then stabilized at a temperature that corresponds to the structuring of the system in the expected new microemulsion.

According to one embodiment, the second microemulsion of step ii) may be subjected, before being brought into contact with the first microemulsion, to at least one temperature-mediated phase inversion operation.

More particularly, this phase inversion operation comprises at least the steps consisting in:
  increasing the temperature of the second microemulsion up to a temperature $T_2$ above its phase inversion temperature (PIT) in order to obtain a water-in-oil emulsion, followed by reducing the temperature down to a temperature $T_1$, where $T_1<PIT<T_2$ so as to obtain an oil-in-water emulsion again;
  where appropriate, carrying out one or more temperature cycles around the phase inversion zone between $T_1$ and $T_2$; and
  stabilizing said system at a temperature within or close to the phase inversion in order to form a new microemulsion obtained by phase inversion.

As regards the oily phase that can be used to produce this second microemulsion, this may be formed from the oils proposed above for the first microemulsion. This oily phase may or may not be identical to that forming the first microemulsion.

Advantageously, in the method according to the invention, the oily phase of each of the two microemulsions comprises at least a triglyceride, a fatty acid ester or one of their mixtures.

Advantageously, the second microemulsion may incorporate a lipophilic active principle. In this case, the nanocapsules obtained after the method according to the invention will incorporate into their liquid lipid core at least one hydrophilic active agent and at least one fat-soluble active agent.

Formation of Nanocapsules

As indicated above, formation of the expected nanocapsules requires the first microemulsion as defined above to be introduced into the second microemulsion.

For obvious reasons, this step is carried out under conditions compatible with maintaining the first and second microemulsions in a stabilized form.

More precisely, the second microemulsion must be at a temperature compatible with the maintenance of its microemulsion architecture. In general, this state of stability is achieved at a temperature lying within its phase inversion zone, namely between 60° C. and 90° C., particularly between 65° C. and 85° C., most particularly between 70° C. and 75° C., for example about 72° C.

Thus, according to a preferred embodiment in the method according to the invention, the second microemulsion considered for the mixture is, during mixing, at a temperature ranging between 60° C. and 90° C., preferably between 65° C. and 85° C., most particularly between 70° C. and 75° C., for example 72° C.

For reasons of greater stability, the second microemulsion is advantageously maintained at a temperature within the high range of the phase inversion zone, i.e. at a temperature above 75° C., especially between 75° C. and 85° C.

Depending on the phase inversion temperature adopted for the second microemulsion, a water-in-oil or oil-in-water microemulsion architecture may be preferred.

As regards the first microemulsion incorporating at least one hydrophilic active agent, its temperature may also vary with regard to the temperature required to achieve this microemulsion structure, taking into account the various components in question in order to form it.

Consequently, the two microemulsions may be brought into contact with each other, either by both being brought to the same temperature or to similar temperatures, or by being at two different temperatures, respectively.

In the context of the present invention, the term "similar temperatures" is understood to mean two temperatures differing in value from each other by at most only 5%.

Thus, according to one particular embodiment, in the method which is the subject of the invention, the two microemulsions brought into contact with each other may or may not have the same temperature.

According to the first alternative, the temperature in question is generally close to or even that required for achieving a microemulsion state for the second microemulsion or else that corresponding to a phase inversion temperature of the second microemulsion.

As mentioned above, the first microemulsion may be, for its part, produced over a wider temperature range, this depending directly on the choice of components required to form it.

Thus, this first microemulsion may be produced between 20 and 80° C., for example at 37° C. or at room temperature.

In the context of the present invention, the term "room temperature" is understood to mean a temperature of about 25° C.

This embodiment at a temperature varying from room temperature to 37° C., especially at room temperature, is most particularly advantageous for encapsulating the heat-sensitive active agent.

By way of example, of one particular embodiment of a method according to the invention, mention may in particular be made of that method consisting in bringing a first microemulsion formed from an oily phase containing Labrafac®, stabilized by a lipophilic surfactant such as Lipoid® and from a hydrophilic phase comprising only propylene glycol or comprising a water/propylene glycol mixture in a 1:3 ratio, into contact with a second microemulsion formed from water, Labrafac® and NaCl, said second microemulsion being stabilized by a heat-sensitive hydrophilic surfactant such as Solutol® and the temperature of which, adopted for forming it, is generally a temperature of about 70° C., for example 72° C. It may then be preferable to heat the first emulsion to a temperature that may be between 65° C. and 80° C., especially between 70° C. and 75° C., for example 72° C. The two microemulsions in this case will be brought to the same temperature or to similar temperatures when they are brought into contact with each other.

Whatever the case may be, it should be noted that the operation of bringing a first microemulsion containing a heat-sensitive active agent into contact with a second microemulsion, requiring for its part to be for example at a temperature of at least 65° C., in order to stabilize its microemulsion architecture, does not prejudice the stability of said active agent. This is because the chill-hardening carried out immediately after the mixing step effectively minimizes the time that this active agent is in contact with such a temperature.

The mixing of the two microemulsions considered according to the present invention generally takes place with mechanical stirring in order to homogenize the two microemulsions.

Advantageously, the two microemulsions mixed in step iii) of the method according to the invention have a weight ratio propitious for stabilizing the second microemulsion.

More particularly, the two microemulsions according to the present invention are brought into contact with each other in a (second microemulsion/first microemulsion containing the active agent) weight ratio propitious for stabilizing the second emulsion, in particular a ratio of between 2 and 20, preferably between 3 and 15, for example about 5.

The merging of the two microemulsions or even their homogenization, may be observed with the naked eye (clear solution).

The novel microemulsion architecture thus formed subsequently undergoes a chill-hardening step according to the invention.

This step for forming the nanocapsules according to the invention consists in suddenly cooling the microemulsion architecture to a temperature suitable for solidifying the interfacial films making up the microemulsion. This temperature is generally well below the phase inversion temperature of the second microemulsion. Advantageously, the cooling takes place with magnetic stirring.

For example, the chill-hardening of said microemulsion charged with one or more active agents may be carried out at a temperature at least 30° C. below the PIT (phase inversion temperature) of the second emulsion during chill-hardening.

This chill-hardening may be carried out by diluting the medium between threefold and tenfold with deionized water at 2° C.±1° C. added into the fine microemulsion. The nanocapsules obtained are kept stirred for 5 minutes.

The organization of the system in the form of nanocapsules after chill-hardening is reflected visually by a change in appearance of the initial system, which changes from transparent white to translucent white with a Tyndall effect (blueish tints). This change occurs at a temperature below the PIT, said temperature generally being between 6 and 15° C. below the PIT.

After the method according to the invention has been completed, nanocapsules charged with at least one active agent according to the invention are obtained.

In the context of the invention, the expression "charged with an active agent" means that the nanoparticles obtained after the method according to the invention has been completed contain, internally, at least one active agent having a hydrophilic character according to the invention within the liquid lipid core thereof.

As mentioned above, the method according to the invention is particularly advantageous for easily and quickly charging the lipid core of a microemulsion with a hydrophilic active agent, which process cannot be achieved by conventional methods.

The hydrophilic active agent is contained in the lipid core in the form of a hydrophilic micellar structure or else a microemulsion having a water-in-oil character, comprising an oily phase stabilized by at least one lipophilic surfactant and a hydrophilic phase incorporating said active agent.

The nanocapsules of the invention are more particularly suitable for the administration of the following active principles: antiseptic agents; proteins, including those involved in the phenomenon of coagulation; peptides; DNA plasmids; SiRNAs; anti-infection agents such as, for example, antifungal agents; antibiotics; anticancer agents; immunosuppressants; active principles intended for the central nervous system, which have to cross the blood-brain barrier, such as anti-Parkinsonian agents; analgesics; and more generally, active principles for treating neurodegenerative diseases.

The active agent encapsulation according to the invention in the nanocapsules according to the invention may be measured by determining the encapsulation yield.

The encapsulation yield EY (in %) of the nanocapsules obtained according to the present invention corresponds to the proportion of active agent present in the nanocapsules relative to the total active agent added to the formulation.

More precisely, this yield is calculated according to the following formula:

$$EY(\%) = (\text{quantity of active agent in the nanocapsules} \times 100)/(\text{quantity of active agent in the nanocapsules} + \text{quantity of free active agent}).$$

The internalized dose of the active agent according to the invention may be measured by spectrophotometry, for example using a spectrophotometer that measures the optical density at a wavelength of 633 nm.

Advantageously, the EY is at least 10%, in particular between 15% and 35%, more particularly between 35% and 100%, preferably between 35% and 80%, in particular between 40% and 60%, for example, 50%.

In the context of the invention, the term "nanocapsules" should be distinguished from nanospheres. The term "nanocapsules" means particles formed from a core that is liquid or semiliquid at room temperature, coated with a film that is solid at room temperature, as opposed to nanospheres, which are matrix particles, i.e. all of the mass is solid. Thus, when the nanospheres contain a pharmaceutically active principle, it is finely dispersed in the solid matrix.

Advantageously, the nanocapsules obtained according to the invention have a mean size of less than 150 nm, preferably less than 100 nm and more preferably less than 50 nm. These sizes may be determined by photon correlation spectroscopy, scanning electron microscopy, or transmission electron microscopy in cryoscopic mode.

The thickness of the solid film is advantageously between 2 and 10 nm. It is also about a tenth of the diameter of the particles. This thickness may be calculated by mass balance, or visualized by negative-shadow transmission electron microscopy or alternatively by transmission electron microscopy in cryoscopic mode.

Given their size, the nanocapsules of the invention are colloidal lipid particles.

The polydispersity index of the nanocapsules of the invention is advantageously between 5% and 15%. This index is determined on the size histogram obtained via the photon correlation spectroscopy method.

The nanocapsules are each formed from an essentially lipid core that is liquid or semiliquid at room temperature, coated with a shell that is solid or semisolid at room temperature.

For the purposes of the invention, the term "essentially lipid" means that the core forming the nanocapsules according to the invention is formed from more than 50% by weight, in particular more than 75% by weight, especially more than 80% by weight, or even more than 90%, more particularly more than 95% of its respective weight, or even totally, from one or more lipid (hydrophobic) compounds.

In the context of the invention, the term "room temperature" denotes a temperature ranging from 18 to 25° C.

Thus, the present invention also relates to nanocapsules having a liquid lipid core and a solid shell and being charged within their lipid core with at least one active agent having a hydrophilic, in particular water-soluble, character, said active agent being present therein in the form of a microemulsion having a water-in-oil character, comprising an oily phase stabilized by at least one lipophilic surfactant and a hydrophilic phase incorporating said active agent.

According to one preferred embodiment, said active agent therein is in a form different from a reverse micellar system.

EXAMPLES

The subject of the present invention is also compositions containing said nanocapsules. The present invention is illustrated by the following examples that are given by way of non-limiting illustration of the scope of the invention.

It should be noted that:
PG=propylene glycol;
IPP=isopropyl palmitate.

EXAMPLE 1

Preparation of a First Microemulsion According to the invention encapsulating Fondaparinux Fondaparinux is a pentasaccharide of the general formula $C_{31}H_{43}N_3Na_{10}O_{49}S_8$ corresponding to:

Its solubility in water is greater than 12.5 mg/ml (concentration of Fondaparinux in its brand form Arixtra®).

To formulate this microemulsion, the hydrophilic phase was made up of only propylene glycol (Patel et al, *J. Agric. Food Chem.* 2006, 54, 7817-7824). The microemulsion also comprised an oily phase (Labrafac® CC, a mixture of $C_8$ and $C_{10}$ triglycerides) and a fat-soluble surfactant (Lipoid® S75-3).

Figure 3:
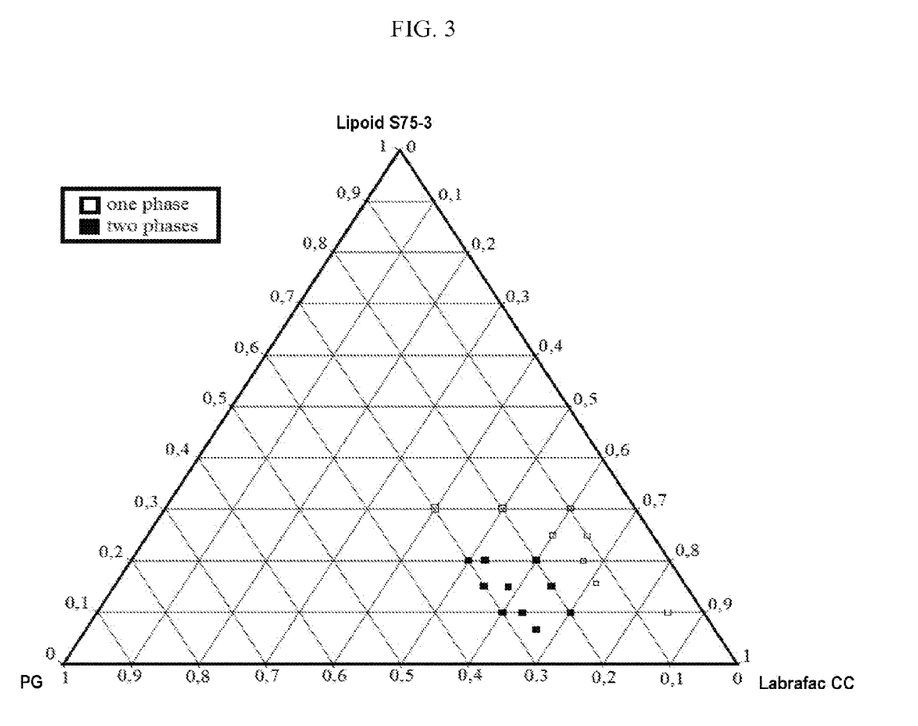
FIG. 3: propylene glycol/Labrafac® CC/Lipoid® S75-3 ternary phase diagram described in Example 1.

The following general protocol was adopted for generating the propylene glycol/Labrafac® CC/Lipoid®S75-3 ternary phase diagram, leading to the characterization of the single-phase zones of microemulsion type, this diagram being shown in FIG. 3.

The Fondaparinux was dissolved in propylene glycol at 75° C. Once they had dissolved, the Lipoid® S75-3 and Labrafac® CC were added and the mixture heated to 75° C. in order to obtain a clear phase, which was kept at this temperature until it was incorporated into the lipid nanocapsules.

A microemulsion was formed in particular by combining 185 mg of oily phase (Labrafac®), 40 mg of propylene glycol, 40 mg of surfactant (Lipoid® S75-3) and 500 of Fondaparinux.

270 mg of a microemulsion formed from 70% oily phase, 15% hydrophilic phase and 15% surfactant, were obtained.

EXAMPLE 2

Formulation of the Microemulsion of Example 1 in the Lipid nanocapsule state In a 20 ml flask, were mixed 504 mg of Solutol® HS15, 44 mg of NaCl, 504 mg of Labrafac® CC and 1.538 g of demineralized water. Three temperature cycles of between 60° C. and 92° C. were carried out. After the third temperature rise, the medium was cooled to 72° C. The medium corresponds to the second microemulsion in question according to the invention.

200 µl of the microemulsion obtained according to example 1 (i.e. about 190 mg), heated to this same temperature, were added with stirring to this second microemulsion, quickly and in one go.

The resulting mixture remained transparent.

A chill-hardening step was then carried out at 70° C., by adding 8 ml of iced water.

The quantity of unencapsulated Fondaparinux was determined by the spectrophotometric method of complexing with the azide A. (Cadene, M. et al, <<J. biol. Chem.>> 1995, 270, 13204-13209).

This thus resulted in a formulation comprising liquid nanocapsules encapsulating the Fondaparinux with a concentration of about 100 µg of Fondaparinux per gram of lipid nanocapsules, i.e. an EY of about 35 to 40%.

EXAMPLE 3

Alternative Formulation of Fondaparinux-Charged Nanocapsules

In a first step, a first microemulsion according to the invention encapsulating Fondaparinux was prepared, by analogy with the method of preparation according to example 1, but in which the Fondaparinux was dissolved beforehand in 3.5 mg of water.

Next, 11.5 mg of propylene glycol were added, the resulting polar phase thus being formed by a ⅓ water/propylene glycol mixture. Once dissolved, 37.5 mg of Lipoid® S75-3 and 97.5 mg of Labrafac® CC were also added to the aforementioned mixture. This was all heated to 75° C. The rest of the procedure was analogous to that described in example 1. 150 mg of microemulsion were obtained and this, after being heated to 75° C. was completely incorporated into a second microemulsion prepared in accordance with the protocol described in example 2, for its part at a temperature of 72° C.

Figure 4:
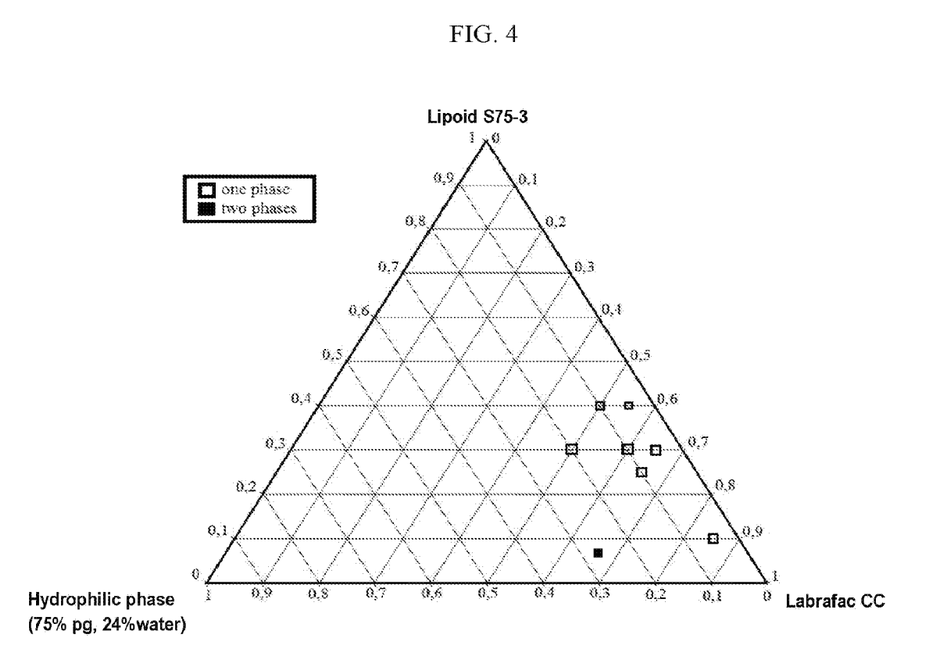
FIG. 4: example of a ternary phase diagram of a microemulsion system described in Example 3.

The parameters involved in this first microemulsion are the same as those indicated in example 1 (FIG. 4).

By analogy with the operating mode described in example 2, the first microemulsion containing the active agent according to the invention was added to the second microemulsion.

What was reproducibly obtained was a formulation consisting of lipid nanocapsules encapsulating Fondaparinux with a concentration of about 50 µg of Fondaparinux per gram of lipid nanocapsules, i.e. an EY of about 15 to 25%.

EXAMPLE 4

Alternative Formulation of Fondaparinux-Charged Nanocapsules

In a first step, a first microemulsion according to the invention encapsulating Fondaparinux, was produced by analogy with the method of preparation described in example 1, involving in the present case 3 mg of Fondaparinux, but in which the Fondaparinux was dissolved beforehand in water (15 mg).

Next, the Labrafac® CC (35 mg), Imwitor® 308 (35 mg) and Span® 60 (15 mg) were added and all heated to 37° C. in order to obtain a clear microemulsion. This microemulsion was kept at 37° C. until being incorporated into the second emulsion.

The second microemulsion was prepared according to the protocol described in example 2, except that it was obtained at a temperature of 78° C.

By analogy with the operating mode described in example 3, 71 mg of the first microemulsion, at a temperature 37° C. containing the active agent, were added to 1 g of the second microemulsion at a temperature of 78° C.

This thus resulted in a formulation comprising lipid nanocapsules encapsulating the Fondaparinux with a concentration of about 3000 µg of Fondaparinux per gram of lipid nanocapsules, i.e. an EY of 100%.

This dose was quantitatively confirmed by chromogenic anti-Xa activity assay,

EXAMPLE 5

Alternative Formulation of Fondaparinux-Charged Nanocapsules

In a first step, a first microemulsion according to the invention encapsulating Fondaparinux, was produced by analogy with the method of preparation described in example 1, employing in the present case 1 mg of Fondaparinux, but in which the Fondaparinux was dissolved beforehand in water (10 mg).

Next, the Labrafac® CC (37.6 mg), Tween 80® (40 mg) and Capmul® MCM (12.5 mg) were added and all was left to equilibrate at room temperature for a few hours in order to obtain a clear microemulsion. This microemulsion was kept at room temperature until being incorporated into the second emulsion.

The second microemulsion was in accordance with that described in example 2, except that it was obtained at a temperature of 80° C.

By analogy with the operating mode described in example 3, 83 mg of the first microemulsion containing the active agent at room temperature were added to 1 g of the second microemulsion at a temperature of 72° C.

This thus resulted in a formulation comprising lipid nanocapsules encapsulating Fondaparinux with a concentration of about 350 µg of Fondaparinux per gram of lipid nanocapsules, i.e. an EY of about 35%.

This preparation mode employing a first microemulsion containing the active agent at room temperature is particularly advantageous for encapsulating an active agent having a hydrophilic, heat-sensitive, water-soluble character.

EXAMPLE 6

Alternative Formulation of Fondaparinux-Charged Nanocapsules

In a first step, a first microemulsion according to the invention encapsulating Fondaparinux, was prepared by analogy with the method of preparation described in example 1, employing in the present case 1 mg of Fondaparinux, but in which the Fondaparinux was dissolved beforehand in water (20 mg).

Next, the Labrafac® CC (37.4 mg), Tween 80® (35 mg) and Lipoid® S75 (12.5 mg) were added and all was heated to 75° C. in order to obtain a clear microemulsion, similar to that described in example 1.

The second microemulsion was in accordance with that described in example 2, except that it was obtained at a temperature of 80° C.

By analogy with the operating mode described in example 3, 20 mg of the first microemulsion containing the active agent at 75° C. were added to 1 g of the second microemulsion at 72° C.

This thus resulted in a formulation comprising lipid nanocapsules encapsulating the Fondaparinux with a concentration of about 100 μg of Fondaparinux per gram of lipid nanocapsules, i.e. an EY of about 50%.

The invention claimed is:

1. A method for preparing nanocapsules composed of (a) a liquid lipid core containing at least one hydrophilic active agent and (b) an solid shell, comprising:
   (A) mixing (1) a first water-in-oil microemulsion comprising a hydrophilic phase comprising at least one hydrophilic active agent and at least one lipophilic surfactant and (2) a second water-in-oil microemulsion comprising at least one heat-sensitive, nonionic hydrophilic surfactant to form (3) a third microemulsion in which the hydrophilic active agent remains in the hydrophilic phase of the first microemulsion,
   wherein the second microemulsion is formulated by phase inversion; and
   (B) chill-hardening the third microemulsion to obtain nanocapsules comprising (i) a lipid core which is liquid at room temperature and comprises the hydrophilic active agent in the form of hydrophilic microdomains or of a water-in-oil microemulsion comprising an oily phase stabilized by at least one lipophilic surfactant and a hydrophilic phase incorporating the hydrophilic active agent and (ii) an encapsulating film that is solid at room temperature.

2. The method of claim 1, wherein the first microemulsion is at a temperature from room temperature to 75° C. during mixing.

3. The method of claim 1, wherein the first microemulsion and the second microemulsion have the same temperature during the mixing.

4. The method of claim 1, wherein the first microemulsion and the second microemulsion have different temperatures during the mixing.

5. The method of claim 1, wherein the hydrophilic phase of the first microemulsion is formed entirely or partly from water, or entirely or partly from at least one polar solvent, or from a water/polar solvent mixture.

6. The method of claim 5, wherein the polar solvent is at least one chosen from the group consisting of polypropylene glycols, propylene glycol, ethanol, isopropanol, glycerol, glycofurol, low-molecular weight polyethylene glycols, and polyols.

7. The method of claim 4, wherein the lipophilic surfactant comprises at least one phospholipid.

8. The method of claim 1, wherein an oily phase of each of the first microemulsion and the second microemulsion comprises an oily phase constituent selected from the group consisting of a triglyceride and a fatty acid ester.

9. The method of claim 1, wherein the first microemulsion comprises a fatty acid triglyceride, a lecithin, a 2-hydroxystearate derivative of polyethylene glycol and the hydrophilic active agent.

10. The method of claim 1, wherein the heat-sensitive, nonionic hydrophilic surfactant comprises a hydrophilic surfactant having an HLB value ranging from 10 to 18.

11. The method of claim 10, wherein the hydrophilic surfactant has an HLB value ranging from 10 to 16.

12. The method of claim 1, wherein the heat-sensitive, non ionic hydrophilic surfactant is selected from the group consisting of ethoxylated fatty alcohols, ethoxylated fatty acids, partial glycerides of ethoxylated fatty acids, triglycerides of fatty acids and ethoxylated derivatives thereof and mixtures thereof.

13. The method of claim 1, wherein the second microemulsion is subjected to at least one temperature-mediated phase inversion operation prior to mixing with the first microemulsion.

14. The method of claim 13, wherein the temperature-mediated phase inversion operation comprises:
   a) increasing the temperature of the second microemulsion up to a temperature L above its phase inversion temperature (PIT) in order to obtain a water-in-oil emulsion, followed by reducing the temperature down to a temperature $T_1$, where $T_1 < PIT < T_2$ so as to obtain an oil-in-water emulsion;
   b) carrying out at least one temperature cycle around the phase inversion temperature between the temperatures $T_1$ and $T_2$ as needed to obtain the oil-in-water emulsion; and
   c) stabilizing the second microemulsion at a temperature at or close to the phase inversion temperature to form a new microemulsion obtained by the temperature-mediated phase inversion operation.

15. The method of claim 1, wherein the first microemulsion and the second microemulsion are mixed in a weight ratio sufficient to stabilize the second microemulsion.

16. The method of claim 15, wherein the weight ratio is between 2 and 20.

17. The method of claim 16, wherein the weight ratio is between 3 and 15.

18. The method of claim 1, wherein the hydrophilic active agent is least one member selected from the group consisting of a pharmaceutically active compound, a cosmetically active compound and a compound that is active in the plant protection or food sector.

19. The method of claim 1, wherein the second microemulsion is at a temperature of between 70° C. and 75° C. during the mixing.

* * * * *